United States Patent
Martin

(10) Patent No.: US 11,883,613 B2
(45) Date of Patent: Jan. 30, 2024

(54) SUCTION CATHETER CLAMP

(71) Applicant: Johnathan Martin, Lafayette, IN (US)

(72) Inventor: Johnathan Martin, Lafayette, IN (US)

( * ) Notice: Subject to any disclaimer, the term of this patent is extended or adjusted under 35 U.S.C. 154(b) by 0 days.

(21) Appl. No.: 17/453,706

(22) Filed: Nov. 5, 2021

(65) Prior Publication Data

US 2022/0143369 A1     May 12, 2022

Related U.S. Application Data

(60) Provisional application No. 63/111,685, filed on Nov. 10, 2020.

(51) Int. Cl.
*A61M 25/02*     (2006.01)
*F16B 2/10*     (2006.01)
*F16B 2/18*     (2006.01)
*F16B 2/00*     (2006.01)
*F16B 2/22*     (2006.01)

(52) U.S. Cl.
CPC ............. *A61M 25/02* (2013.01); *F16B 2/005* (2013.01); *F16B 2/10* (2013.01); *F16B 2/185* (2013.01); *F16B 2/22* (2013.01); *A61M 2025/024* (2013.01)

(58) Field of Classification Search
CPC . A61M 25/02; A61M 2025/024; F16B 2/005; F16B 2/10; F16B 2/185; F16B 2/22; Y10T 24/44385; Y10T 24/4447
USPC ............. 248/689; 24/3.11, 3.12, 229.13, 338
See application file for complete search history.

(56) References Cited

U.S. PATENT DOCUMENTS

| | | | | |
|---|---|---|---|---|
| 556,209 | A | * 3/1896 | Quinn | A45F 5/02 |
| | | | | 24/339 |
| 2,499,517 | A | * 3/1950 | Marini | D06F 55/00 |
| | | | | 24/334 |
| 2,715,292 | A | * 8/1955 | Williams | A01K 97/06 |
| | | | | 24/507 |
| 4,362,402 | A | * 12/1982 | Kallinke | G04B 37/1413 |
| | | | | 248/116 |
| 4,662,039 | A | * 5/1987 | Richardson | A44B 99/00 |
| | | | | 24/511 |

(Continued)

FOREIGN PATENT DOCUMENTS

| | | | | |
|---|---|---|---|---|
| CN | 103189091 A | * | 7/2013 | ........ A61M 16/0057 |
| EP | 2253350 A1 | * | 11/2010 | ........ A61M 16/0875 |

(Continued)

*Primary Examiner* — Kimberly T Wood
(74) *Attorney, Agent, or Firm* — Maginot, Moore & Beck, LLP

(57) ABSTRACT

A suction catheter clamp is provided for supporting a suction catheter on a structure in an operating room, such as an IV pole or a bed frame. The clamp includes a pair of legs terminating at one end in opposing jaws and defining an opening between the jaws. The legs are pivotably connected to each other so that the opposing jaws can move apart to enlarge the opening to receive the structure and are biased towards each other to engage and clamp onto the structure. A resilient clip is defined on one leg of the pair of legs that is configured to receive and clamp a suction catheter between the resilient clip and a surface of the one leg. The clamp also includes a retainer defined on the other leg of the pair of legs that is configured to receive and crimp a tube that is to be connected to the suction catheter.

5 Claims, 8 Drawing Sheets

(56) References Cited

U.S. PATENT DOCUMENTS

| | | | | |
|---|---|---|---|---|
| 5,148,981 | A * | 9/1992 | Lynch, Jr. | E01B 9/306 238/349 |
| D408,097 | S * | 4/1999 | Heydt | D8/395 |
| 5,975,092 | A * | 11/1999 | Tsai | A45D 8/20 132/273 |
| 6,189,542 | B1 * | 2/2001 | Shepard | A45D 8/20 132/273 |
| 6,477,744 | B1 * | 11/2002 | Miles | B43K 23/002 24/3.12 |
| 6,523,231 | B1 * | 2/2003 | Lassiter | H02G 3/30 24/339 |
| 8,356,784 | B2 * | 1/2013 | Doll | F16M 13/022 248/316.1 |
| 8,733,710 | B1 * | 5/2014 | Suazo | H02G 3/32 248/74.1 |
| 8,955,510 | B2 * | 2/2015 | Youngblood | F16L 3/237 128/200.24 |
| 8,974,421 | B1 * | 3/2015 | Khalaj | A61M 25/02 604/174 |
| 9,016,510 | B2 * | 4/2015 | Edwards | A47G 23/02 220/574.1 |
| 9,237,820 | B2 * | 1/2016 | Forbes | A47G 33/08 |
| 9,695,849 | B2 * | 7/2017 | Zhou | F16M 11/041 |
| 9,788,673 | B2 * | 10/2017 | Gschwind, Jr. | A47G 23/0225 |
| 9,980,612 | B2 * | 5/2018 | Neumann | F16M 13/022 |
| 10,208,874 | B2 * | 2/2019 | Geiger | H02S 30/00 |
| 10,785,554 | B2 * | 9/2020 | Mainini | A45F 5/02 |
| 10,847,960 | B1 * | 11/2020 | Naugler | F16B 2/22 |
| D922,831 | S * | 6/2021 | Luke | D7/708.1 |
| 2003/0188403 | A1 * | 10/2003 | Lemke | A61M 16/0683 24/338 |
| 2004/0045133 | A1 * | 3/2004 | Buettell | A45F 5/02 24/3.12 |
| 2010/0115739 | A1 * | 5/2010 | Mathur | A45F 5/02 24/304 |
| 2012/0012723 | A1 * | 1/2012 | Mansfield | A24F 1/30 248/230.8 |
| 2012/0272483 | A1 * | 11/2012 | Moore | F16B 2/22 24/3.12 |
| 2012/0305721 | A1 * | 12/2012 | Lin | D06F 55/02 248/224.8 |
| 2013/0192032 | A1 * | 8/2013 | Huang | H02G 3/32 24/594.1 |
| 2019/0029404 | A1 * | 1/2019 | Mainini | F16B 2/22 |

FOREIGN PATENT DOCUMENTS

| | | | | |
|---|---|---|---|---|
| WO | WO-2012059840 | A1 * | 5/2012 | A61M 16/0057 |
| WO | WO-2014110112 | A1 * | 7/2014 | A45F 5/02 |

* cited by examiner

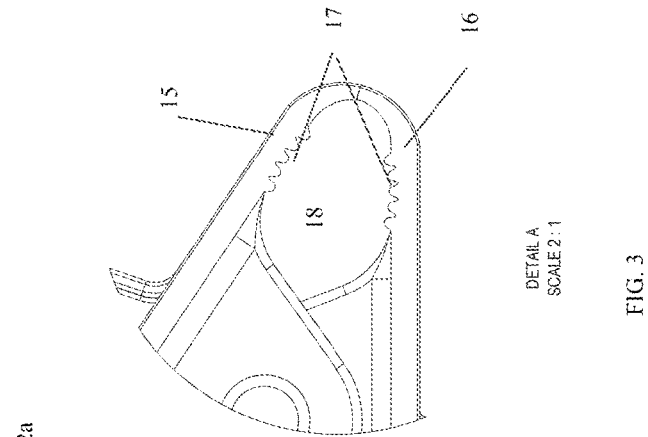
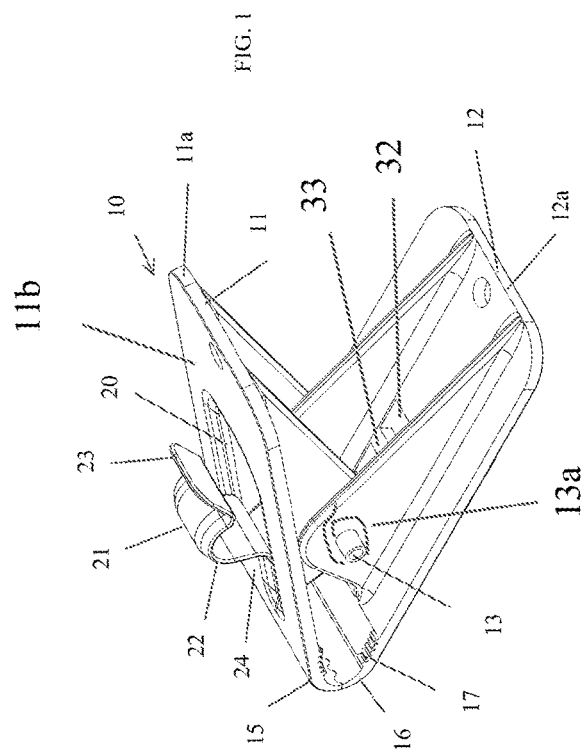
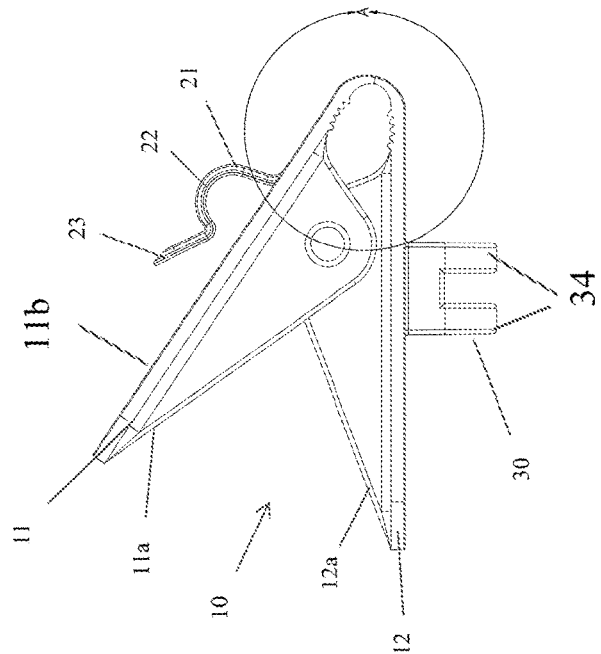

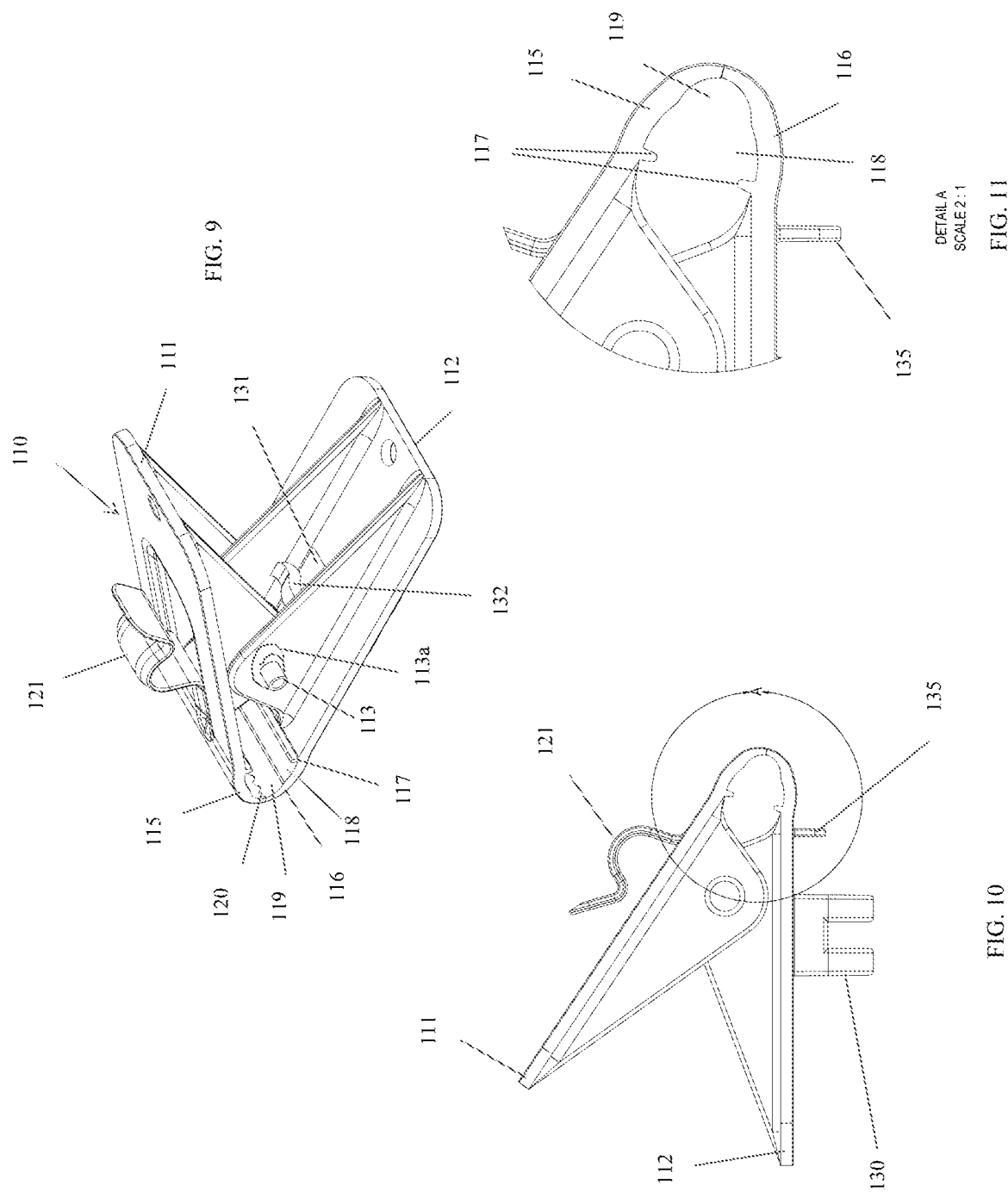

SUCTION CATHETER CLAMP

PRIORITY CLAIM

This application is a utility filing from and claims priority to U.S. Provisional Application No. 63/111,685, which was filed on Nov. 10, 2020, the entire disclosure of which is incorporated herein by reference.

BACKGROUND

Oral suction catheters are used during medical procedures to suction out a patient's mouth and oral pharynx. The removed material can vary from saliva, blood, mucus, gastric contents, and foreign bodies. A suction catheter or wand is connected to a canister for collecting the fluids. The canister is connected to a vacuum source to draw the fluids through the catheter and into the canister. In a typical operating room, the tubing associated with the suction system is part of a jumbled array of wires and tubes needed to perform the surgery.

Since oral suction is needed on command at any time during the procedure, the suction system S is kept activated throughout the procedure and held in a protective wrapper until needed. Unless the suction catheter is clamped off air is drawn continuously into the suction system S. The suction sound can be very loud and distracting, so one practice is to clamp off the catheter to prevent air from being drawn into the system. This often involves kinking the suction tubing between the catheter and the canister in some manner. Moreover, this action usually results in the wrapper falling off the catheter which risks contaminating the catheter. In some cases, the suction catheter is wedged under the mattress of the procedure table, which carries its own set of risks.

There is a need for a device that can clamp off the suction catheter while keeping the catheter in its protective wrapper. There is also a need for a device that can keep the suction catheter close at hand without becoming entangled in the array of wires and tubes in the procedure room.

SUMMARY OF THE DISCLOSURE

A suction catheter clamp is provided for supporting a suction catheter on a structure in an operating room, such as an IV pole or a bed frame. The clamp comprises a pair of legs terminating at one end in opposing jaws and defining an opening between the jaws. The legs are pivotably connected to each other so that the opposing jaws can move apart to enlarge the opening to receive the structure and towards each other to engage the structure. The clamp includes a biasing element that is configured to bias the opposing jaws towards each other to clamp onto the structure.

In one aspect, a resilient clip is defined on one leg of the pair of legs that is configured to receive a suction catheter. The resilient clip is configured to clamp the suction catheter between the clip and a surface of the one leg. The clip thus holds the suction catheter in a convenient location but free of the array of wires and tubes normally found in an operating room.

In another feature, the clamp includes a retainer defined on the other leg of the pair of legs. The retainer defines a bore to receive a tube apart from the suction catheter and is configured to crimp the tube. One end of the tube is connected to a suction source, but the crimp feature of the retainer prevents the flow of air through the tube. This allows the suction to remain on and available when the tube is removed from the retainer and engaged to the suction catheter prior to its removal from the clamp.

DESCRIPTION OF THE FIGURES

FIG. 1 is a perspective view of a suction catheter clamp according to one embodiment of the present disclosure.

FIG. 2 is a side view of the suction catheter clamp shown in FIG. 1.

FIG. 3 is an enlarged view of the jaws of the clamp shown in FIG. 2.

FIG. 9 is a perspective view of a suction catheter clamp according to another embodiment of the present disclosure.

FIG. 10 is a side view of the suction catheter clamp shown in FIG. 9.

FIG. 11 is an enlarged view of the jaws of the clamp shown in FIG. 10.

DETAILED DESCRIPTION

Figure 5:
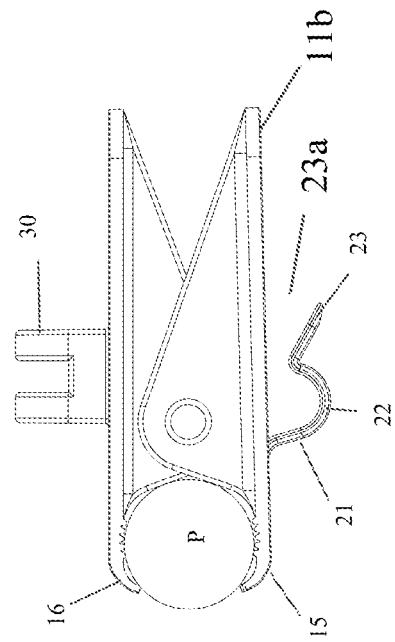
FIG. 5 is a top view of the clamp mounted to the IV pole shown in FIG. 4.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 4:
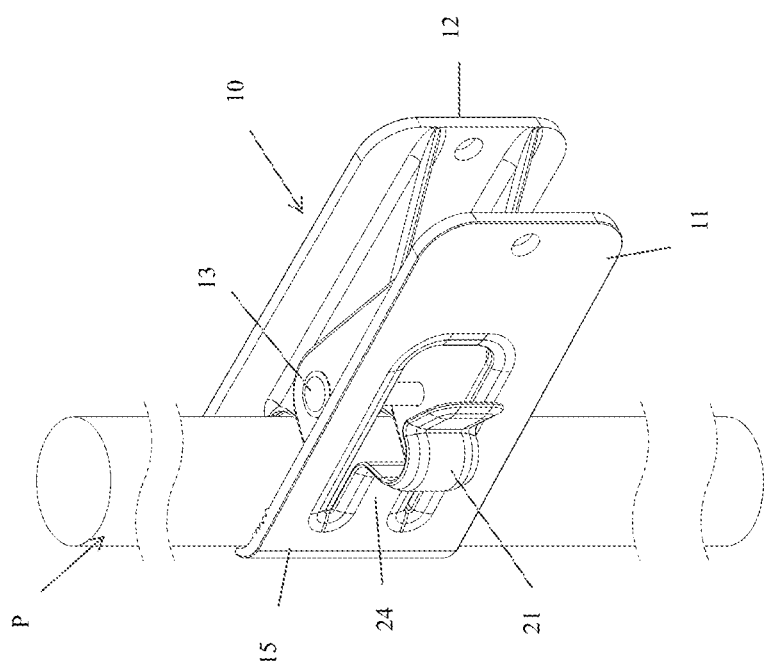
FIG. 4 is a perspective view of the suction catheter clamp of FIG. 1 mounted to an IV pole.

To address the unmet needs regarding suction catheters, a suction catheter clamp 10 is provided as shown in FIG. 1-8. The clamp 10 includes a pair of legs 11, 12, pivotably connected to each other at a pivot 13. The legs terminate in opposing jaws 15, 16 that are biased to the clamped position shown in FIGS. 1-3 by a spring, such as a torsion spring 13a, as known in the art. The opposing jaws 15, 16 define an opening 18 that is sized to fit around an IV pole P when the jaws are at least partially open, as shown in FIGS. 4-5. The jaws each include a gripping surface 17 that can be in the form of teeth, as depicted in FIG. 3, or can be provided in other forms that are capable of gripping an IV pole, such as a high-friction pad. It can be appreciated that the arms 11, 12 are sized so that the jaws 15, 16 can be easily opened by pressing the free ends 11a, 12a toward each other. The clamp is configured and sized so that the jaws can be opened wide enough to accept a standard IV pole. The spring-bias feature of the clamp is strong enough to hold the clamp in position on the IV pole without risk of the clamp sliding down the pole.

The clamp thus far has the attributes of a conventional clip or clamp. It is understood that the legs 11, 12 and jaws 15, 16 can have other configurations that are capable of engaging the clamp 10 to a vertical pole, such as the IV pole P shown in FIGS. 4-5. However, the configuration disclosed herein allows for easy operation—the clamp can be engaged to an IV pole by depressing and releasing the free ends 11a, 12a of the legs with the jaws encircling the pole. In addition, this configuration allows the clamp to be attached to other surfaces and components, such as the main suction line of the canister, a rail of the procedure table, or even the patient pillow.

In one important feature, the clamp 10 is configured to support a suction catheter contained within its protective wrapper. The leg 11 of the clamp defines an opening 20 with a resilient clip 21 disposed therein. The clip 21 includes a curved shell 22 that is sized and configured to engage the suction catheter, such as catheter C in FIG. 8, even when the catheter is contained within a wrapper W. The clip includes a resilient arm 24 affixed to the leg 11 at one end of the opening 20. As shown in FIG. 1, the clip 21 extends along a length of the opening, generally from the jaw 15 toward the free end 11a. The clip also includes a lever 23 that can be used to bend the clip 21 outward away from the opening 20 and from the surface 11b of the leg to allow introduction of the packaged catheter C into the shell 22. As shown in FIG. 5, the lever 23 is angled outward relative to the surface 11b to define an entry space 23a between the lever and the surface. The entry space 23a is sufficiently large to allow the body of the suction catheter to engage the lever as the catheter is pushed into the shell 22, thereby deflecting the lever, and thus the clip 21 outward to receive the catheter. Alternatively, the lever 23 can be manually engaged to deflect the clip to receiver the catheter. The clip 21, and particularly the arm 24, is configured so that the shell is biased toward the opening so that the effective diameter of the opening is reduced when the clip is in its normal configuration. Thus, when a catheter is engaged by the clip the catheter is crimped between the shell 22 and the side edges of the opening 20. The resilient arm 24 is configured to provide a clamping force that is sufficient to secure the catheter and its wrapper.

Figure 8:
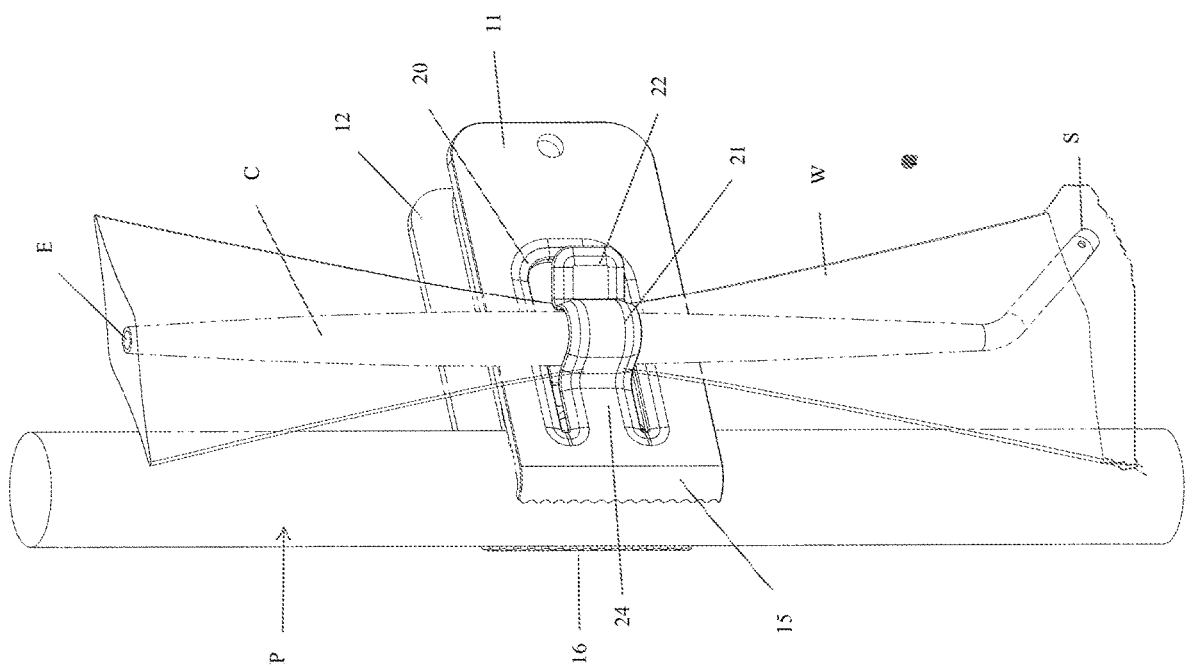
FIG. 8 is a perspective view of the clamp of FIG. 1 mounted to an IV pole and supporting a suction catheter within a protective wrap.

As shown in FIG. 8, the clamp 10 can be mounted on an IV pole P and the packaged catheter C can be secured by the clip 21. The packaged catheter can be easily removed by pulling the packaged catheter outward past the lever 23 so that the clip flexes outward to release the catheter from the shell 22. The packaged catheter can be equally easily introduced into the clip by pushing the catheter against the lever 23 toward the opening, which causes the clip to flex outward to receive the catheter. This process can be repeated as often as necessary during the medical procedure. The IV pole P supports the clamp 10 and the packaged suction catheter C close at hand, and allows the suction catheter to be moved as desired within the procedure room. The clamp 10 allows the suction catheter C to be supported with the suction end S pointed downward to catch any liquid in the wrapper, as shown in FIG. 8.

Figure 7:
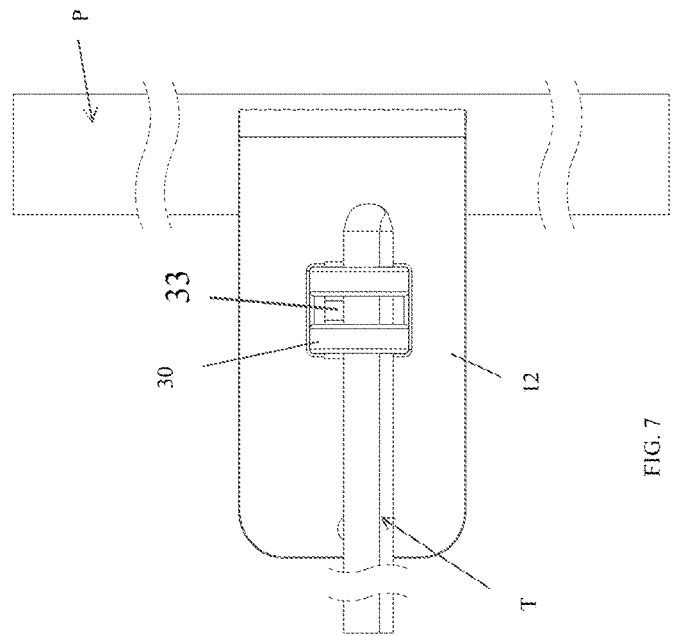
FIG. 7 is a side view of the clamp, IV pole and suction tubing shown in FIG. 6.
Figure 6:
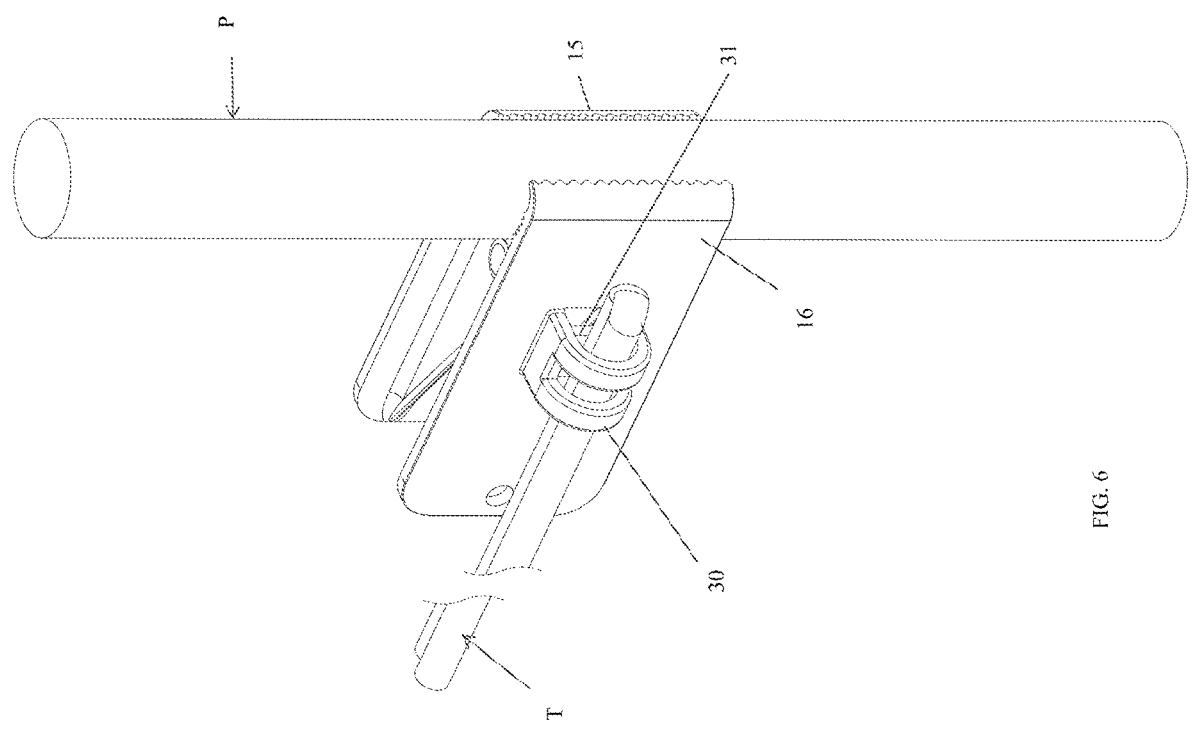
FIG. 6 is perspective view of the clamp of FIG. 1 mounted to an IV pole with suction tubing supported by the clamp.

In another feature of the clamp 10, the suction tubing connected between the canister and the suction catheter can be crimped off, thereby closing the catheter and preventing the flow of air through the catheter. This feature silences the catheter when not in use and also supports the tubing and prevents it from entangling with other wires and tubes. In this feature, the other leg 12 of the clamp includes a tube retainer 30 projecting from the leg. The retainer 30 defines a bore 31 through which a tube T extends, as shown in FIGS. 6-7. The tube retainer is positioned over an aperture 32 in the leg 12. A bridge 33 spans the width of the opening and is flanked on its opposite sides by ring elements 34 of the retainer that define the bore 31, as shown in FIG. 7. The tube T is truncated in FIGS. 6-7, but it is understood that the left end of the tube is connected to the canister while the right end of the tube in the figures is configured to be connected to the connection end E of the suction catheter. The tubing can be crimped in the retainer 30 between the ring elements 34 and the bridge 33. In one approach, the tube is connected to the catheter, so the tube is looped to the connection end E of the catheter (FIG. 8) so that it is kept free of other wires, tubing and equipment. Alternatively, the tubing T can be held by the retainer independent and disconnected from the catheter, until it is removed for engagement to the connection end E of the catheter.

Figure 13:
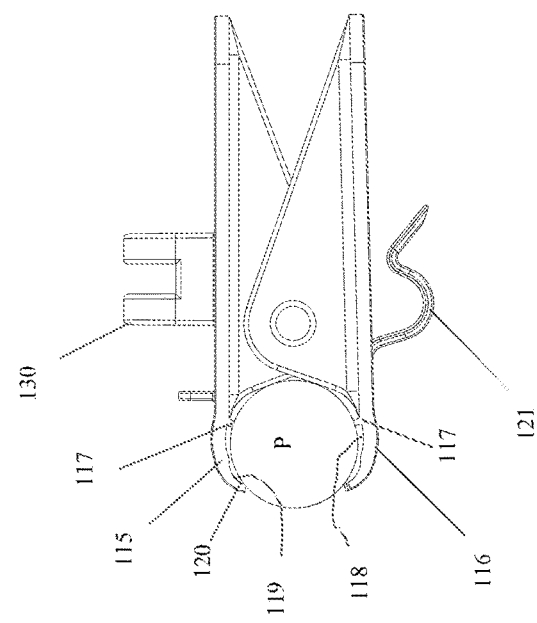
FIG. 13 is a top view of the clamp mounted on the IV pole shown in FIG. 12.
Figure 12:
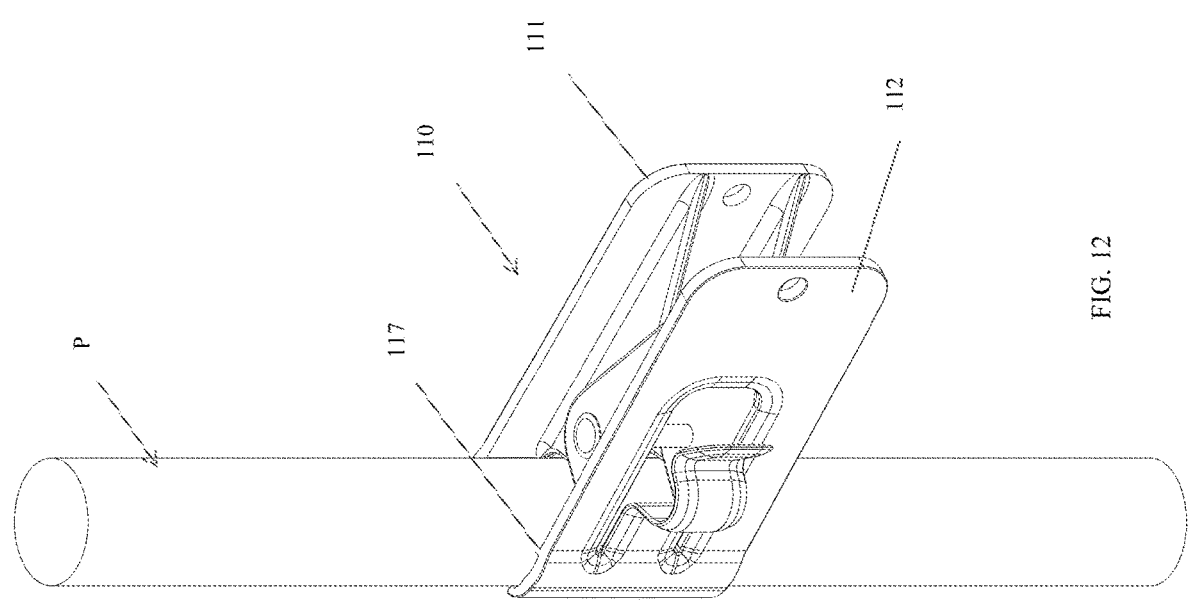
FIG. 12 is a perspective view of the suction catheter clamp of FIG. 9 mounted to an IV pole.
Figure 15:
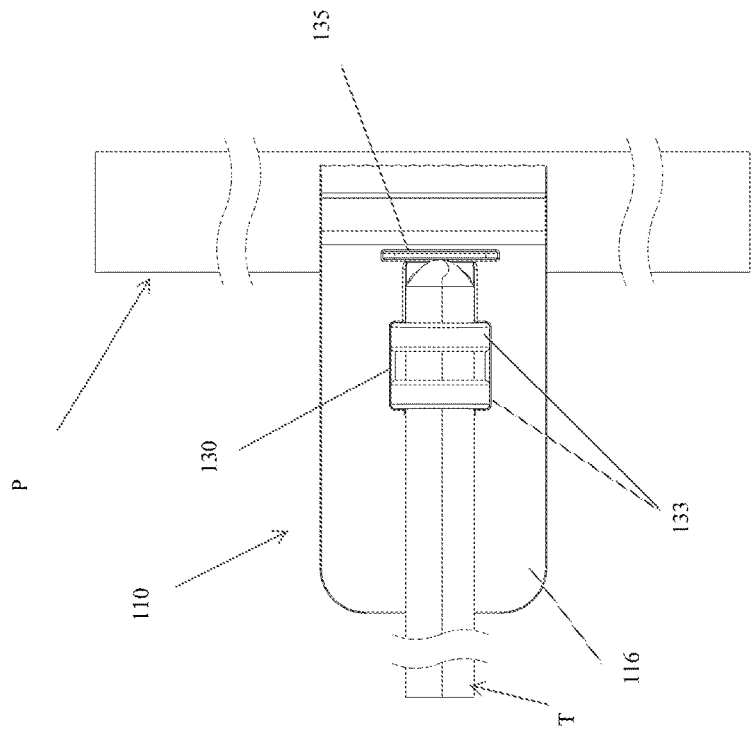
FIG. 15 is a side view of the clamp, IV pole and suction tubing shown in FIG. 14.
Figure 14:
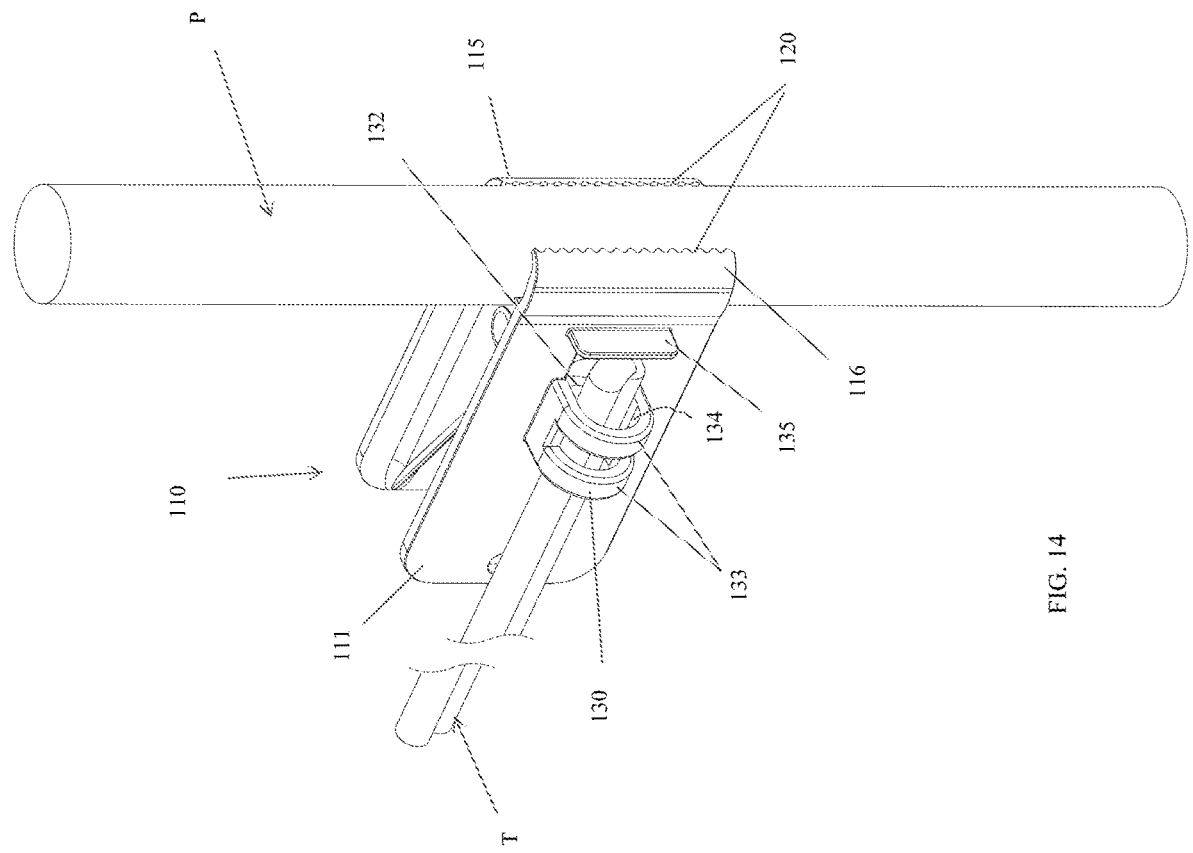
FIG. 14 is perspective view of the clamp of FIG. 9 mounted on an IV pole with suction tubing supported by the clamp.
Figure 16:
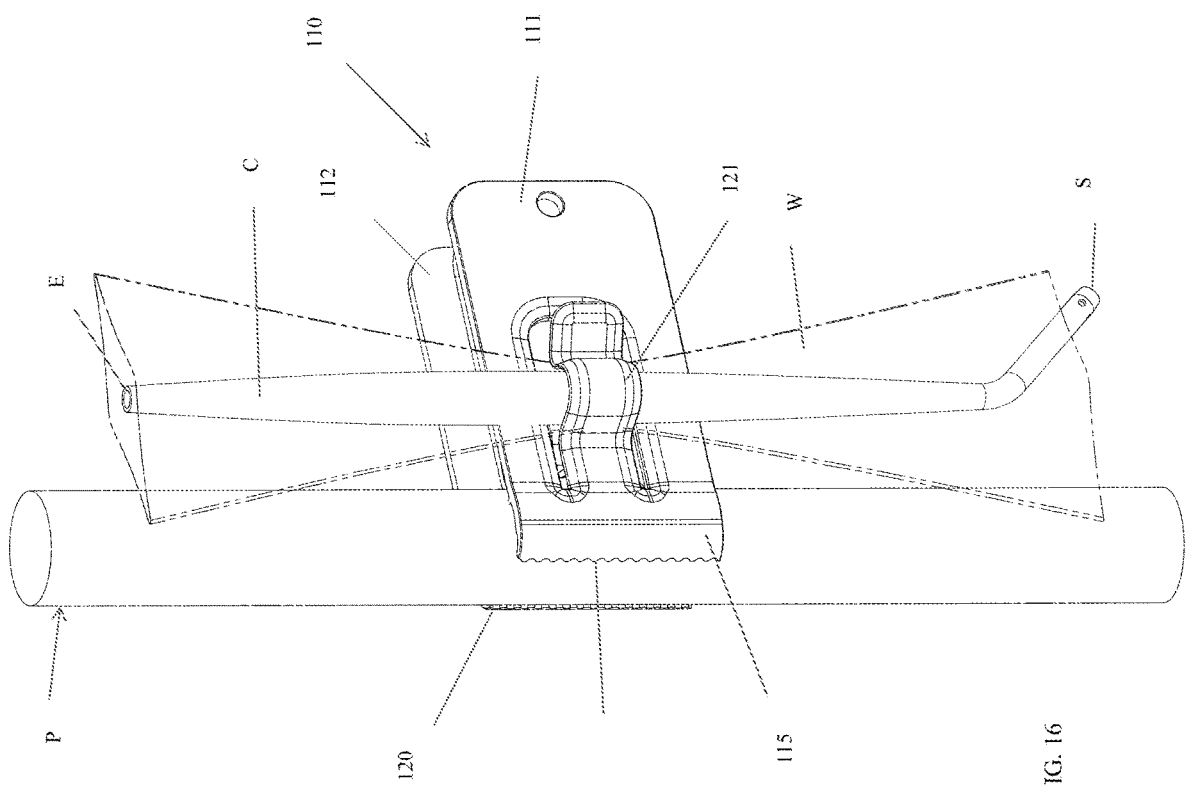
FIG. 16 is a perspective view of the clamp of FIG. 9 mounted on an IV pole and supporting a suction catheter within a protective wrap.

Another embodiment of a suction catheter clamp 110 is shown in FIGS. 9-17. Much of the structure of the clamp 110 is identical to the clamp 10. Thus, the clamp 110 includes a pair of legs 111, 112 that are pivotably connected at a pivot 113. The legs terminate in opposing jaws 115, 116 that are biased to the closed position, such as by a torsion spring 113a or other biasing mechanism known in the art. The opposing jaws 115, 116 define a pair of opening portions 118, 119, with the opening portion 119 adjacent the edge 120 of the jaws. The opening portion 119 of each jaw is defined at an effective radius that is smaller than the effective radius of the opening portion 118 of the jaws, as best seen in FIGS. 11 and 13. The effective radius of the inner opening portion 118 approximates the radius of the IV pole P on which the suction catheter clamp 110 is mounted. The inner opening portion 118 extends from a rib 117 on the inside of each jaw, with the rib 117 configured and arranged to engage the pole P when the clamp is clamped onto the pole. The smaller effective radius of the outboard opening portion 119 allows the edges 120 of the two jaws to engage the pole. In one embodiment, the opposing edges 120 define teeth that can provide an effective grip on the IV pole P, as shown in FIGS. 14 and 16. In this embodiment, the jaws 115, 116 are sized so that the teeth of the edges 120 engage, rather than encircle, the pole. The ends of the jaws at the edges 120 can have a reduced thickness to allow the edges to flex when the clamp engaged the IV pole, to facilitate engagement of the teeth into the pole.

Figure 17:
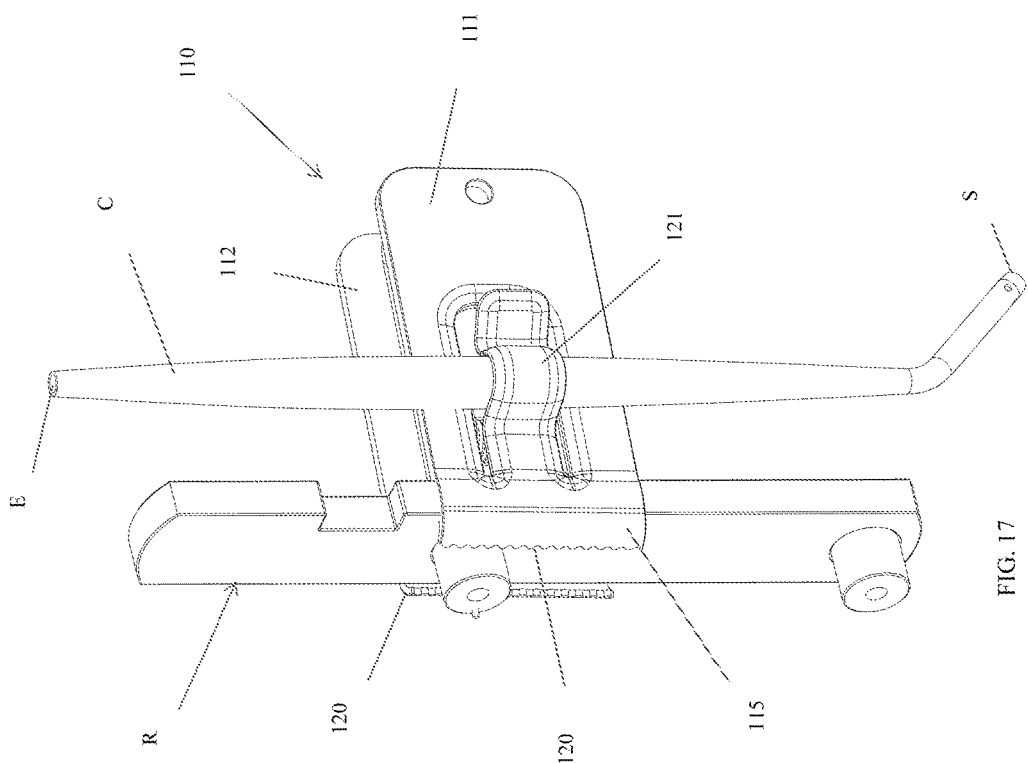
FIG. 17 is a perspective view of the clamp of FIG. 9 mounted on a support structure.

The clamp 110 includes a clip 121 that is substantially identical to the clip 21 described above. Like the clip 21, the clip 121 is resilient so that the clip can be deflected outward to accept a catheter C, as shown in FIG. 16, and then resiliently apply pressure to hold the catheter to the clamp. Thus, like the clip 10, the clamp 121 of the clip 110 can support a suction catheter C in its wrapper W, as shown in FIG. 16. The clamp 121 can also hold the catheter C outside of its wrapper. As shown in FIG. 17, the jaws 115, 116 can engage a bed rail R. In this configuration, the edges 120 of the jaws encircle the rail R, with the edge of the rail engaging the outboard opening portion 119. The ribs 117 also engage the side of the rail, or if the rail is sufficiently narrow can engage the outboard face of the rail.

As in the clamp 10, the clamp 110 includes a tube retainer 130 that can be used to crimp off the catheter tubing when it is disconnected from the catheter C. As shown in FIGS. 9 and 14, the retainer 130 includes an interior bridge 131 spanning an aperture 132 defined in the leg 111. The retainer includes offset ring portions 133 that flank the interior bridge 131. The ring portions 133 define an opening 134 that is sized to receive the tube T therethrough. A wall 135 is offset from the retainer in alignment with the opening to stop the advancement of the tube T through the retainer, as shown in FIG. 15. This ensures that the user does not feed excessive length of the tube into the retainer, which would make it more difficult to remove the tube when it is needed.

In one embodiment, the interior bridge 131 is a resilient clip with an unbiased position intersecting the opening 134 of the ring portions 133. The bridge 131 thus applies pressure to the tube T within the retainer to produce a kink in the tube, thereby closing it off. In another embodiment, the ring portions can be configured so that the tube must be bent inward to pass into the aperture 132 and then bend outward to exit the opening 134. This produces a kink in the tube T to close it off.

The clamps 10 and 110 can be formed of a sterilizable material, such as stainless steel or certain plastics. The legs 11, 12, 111, 112 can be stamped or molded. The tube retainers 30, 130 can be integrally formed with the leg 12, 112 or can be separately formed and attached in a conventional manner. The clamps 10, 110 are sized to be able to clamp and support a conventional suction catheter and associated tubing, but still maintain a small profile to avoid interfering with other components and equipment in the surgical arena.

The present disclosure contemplates a clamp for a suction catheter that is configured to clamp off the suction catheter to prevent air flow even as suction is maintained. The clamp allows the suction catheter to be supported within its protective wrapper on an IV pole or other structure convenient to the medical personnel. A tube retainer crimps the suction tubing and helps keep the suction tube connected to the suction catheter out of the way of other components and equipment while keeping the suction catheter handy and ready for use at any time.

The clamp 10 is described herein for use with an oral suction catheter, such as might be used by an anesthesiologist. However, the clamp can also be used for a suction catheter used for wound irrigation, with appropriate sterile procedures.

The present disclosure should be considered as illustrative and not restrictive in character. It is understood that only certain embodiments have been presented and that all changes, modifications and further applications that come within the spirit of the disclosure are desired to be protected.

What is claimed is:

1. A suction catheter clamp for supporting a suction catheter on a structure in an operating room, the clamp comprising:
   a pair of legs terminating at one end in opposing jaws and defining an opening between the jaws, the legs pivotably connected to each other so that the opposing jaws can move apart to enlarge the opening to receive the structure and towards each other to engage the structure;
   a biasing element configured to bias the opposing jaws towards each other to clamp onto the structure;
   a resilient clip defined on one leg of the pair of legs, the resilient clip;
       configured to receive the suction catheter between the resilient clip and a surface of the one leg; and
       biased toward the surface to clamp the suction catheter to the one leg; and
   a retainer defined on the other leg of said pair of legs, said retainer defining a bore to receive a tube apart from the suction catheter, said retainer configured to crimp the tube, wherein;
   said other leg defines an aperture with a bridge element extending across a width of the aperture; and
   the retainer includes a pair of ring elements defining said bore, said ring elements flanking either side of the bridge element so that the tube can be crimped between said pair of ring elements and said bridge element.

2. The suction catheter clamp of claim 1, wherein each of said jaws includes a gripping surface arranged to grip the structure when the jaws are clamped onto the structure.

3. The suction catheter clamp of claim 2 wherein said gripping surface includes a plurality of teeth.

4. The suction catheter clamp of claim 1, wherein each of said jaws includes an edge defining teeth for engaging the structure when the jaws are clamped onto the structure.

5. The suction catheter clamp of claim 1, wherein each of said jaws includes a rib extending from an inner surface thereof and configured to engage the structure when the jaws are clamped onto the structure.

\* \* \* \* \*